(12) United States Patent
Stanton et al.

(10) Patent No.: US 8,304,190 B2
(45) Date of Patent: Nov. 6, 2012

(54) PHARMACOGENOMICS OF BLOOD PRESSURE LOWERING AGENTS

(75) Inventors: Alice Stanton, Dublin (IE); Niamh Moore, Dublin (IE)

(73) Assignee: Royal College of Surgeons in Ireland, Dublin (IE)

( * ) Notice: Subject to any disclaimer, the term of this patent is extended or adjusted under 35 U.S.C. 154(b) by 958 days.

(21) Appl. No.: 11/883,520

(22) PCT Filed: Feb. 2, 2006

(86) PCT No.: PCT/IE2006/000005
§ 371 (c)(1),
(2), (4) Date: Aug. 13, 2008

(87) PCT Pub. No.: WO2006/082570
PCT Pub. Date: Aug. 10, 2006

(65) Prior Publication Data
US 2009/0325151 A1    Dec. 31, 2009

(30) Foreign Application Priority Data

Feb. 2, 2005   (EP) .................................... 05394002

(51) Int. Cl.
*C12Q 1/68* (2006.01)
*A61P 9/12* (2006.01)

(52) U.S. Cl. ..................... 435/6.11; 514/15.7; 514/15.8; 514/16.2

(58) Field of Classification Search ........................ None
See application file for complete search history.

(56) References Cited

FOREIGN PATENT DOCUMENTS

| WO | 88/08457 | 11/1988 |
|---|---|---|
| WO | 00/22166 | 4/2000 |

OTHER PUBLICATIONS

Fuchs, S. et al. Journal of Hypertension 20(12):2391-2398 (Dec. 2002).*
Moore, N. et al. Journal of Hypertension 22(Suppl 1):S178 (Feb. 2004).*
Arnett, D.K. and Claas, S.A. Drug Development Research 62:191-199 (2004).*
Ng, D.P.K. et al. Clinica Chimica Acta 343:191-194 (2004).*
Jalil, J.E. and Ocaranza, M.P. Revista Espanola de Cardiologia 55(2):89-91 (2002).*
Kurland, L et al. American Journal of Hypertension 17:8-13 (2004).*
Moore, N. et al. Hypertension 50:340-347 (2007).*
Konoshita, T. et al. Journal of Hypertension 22(Suppl 2):S317 (2004).*
Merriam Webster Medical Dictionary, definition of "administering," downloaded from www.merriam-webster.com/medical/ on Jun. 22, 2012 (1 page).*
The Free Dictionary Medical Dictionary, definition of "administering," downloaded from medical-dictionary.thefreedictionary.com on Jun. 22, 2012 (1 page).*
Fuchs Sebastien et al., "Functionality of two new polymorphisms in the human rennin gene enhancer region." *Journal of Hypertensions*, vol. 20, No. 12, Dec. 2002, pp. 2391-2398.
Arnett Donna K. et al., "Pharmacogenetics of antihypertensive treatment," *Drug Development Research*, vol. 62, No. 3, Jul. 2004, pp. 191-199.
Kurland Lisa et al., "Angiotensinogen gene polymorphisms: relationship to blood pressure response to antihypertensive treatment: Results from the Swedish irbesartan left ventricular hypertrophy investigation vs atenolol (SILVHIA) trial," *American Journal of Hypertension*, vol. 17, No. 1, Jan. 2004, pp. 8-13.

* cited by examiner

*Primary Examiner* — Diana Johannsen
(74) *Attorney, Agent, or Firm* — Occhiuti Rohlicek & Tsao LLP

(57) ABSTRACT

A method of determining a suitable blood pressure lowering treatment for an individual comprises a step of assaying a biological sample from the individual for the presence or absence of the C-5312T SNP in a distal enhancer region of the renin gene. The presence of at least one T allele is indicative of an increased response to a blood pressure lowering treatment selected from the group comprising: angiotensin-2-receptor blockers; ACE Inhibitors; aldosterone receptor blockers; and beta-receptor blockers. The absence of at least one T allele is indicative of an increased response to a blood pressure lowering treatment selected from the group comprising: renin inhibitors; calcium channel blockers; and diuretics.

5 Claims, No Drawings

PHARMACOGENOMICS OF BLOOD PRESSURE LOWERING AGENTS

RELATED APPLICATIONS

This application is a national stage filing under 35 U.S.C. §371 of international application PCT/IE2006/000005, filed Feb. 2, 2006, which was published under PCT Article 21 (2) in English.

TECHNICAL FIELD

The invention relates to a method of predicting response to blood pressure (BP) lowering agents. In particular, the invention relates to a method of predicting a response to angiotensin-2-receptor blocker and renin inhibitor classes of BP lowering agents.

BACKGROUND TO THE INVENTION

Since its discovery a century ago, the role of the renin angiotensin aldosterone system (RAAS) as an endocrine system involved in BP and fluid electrolyte regulation has been well established.[1] Recent clinical trial evidence suggests that the RAAS may influence large vessel atherosclerosis and cardiovascular morbidity and mortality independently of Bp[2]. Atheromatous lesions result from an excessive inflammatory-fibroproliferative response to various forms of insult[3]. Through promotion of vasoconstriction, vascular smooth muscle cell growth, inflammation, generation of reactive oxygen species, thrombosis and vascular remodeling, angiotensin II has been identified as a key mediator in the process of atherogenesis.[4]

Renin is of considerable importance as the first and rate limiting step in the RAAS system. It was noted as long ago as 1972 that hypertensive patients with high renin levels were more likely than those with normal or low renin levels to experience myocardial infarcts. Synthesis and secretion of renin by kidney juxtaglomerular cells is upregulated by cAMP, (mainly through beta 1 adrenergic receptor agonism), and down regulated by angiotensin II and intracellular calcium, in response to salt load, renal perfusion pressure, noradrenaline and renal prostaglandins.[5] Several DNA elements in the distal and proximal promoter regions as well as in intron 1 have been implicated in cAMP regulation. A high molecular weight inactive renin is formed when renin combines with its endogenous inhibitor renin binding protein (ReBP).[6]

Dispite renin being the key enzyme of the RAAS system, and therefore a good candidate quantitative trait locus for elucidating the molecular and genetic influences implicated in the molecular etiology of essential hypertension, a consensus concerning the nature, frequency and functionality of SNPs in the renin gene has not yet been reached.[7] A very small sib-pair analysis (66 dizygotic twins and their parents) found both diastolic and systolic BP to be linked to the renin gene locus.[8] However two other linkage studies yielded negative results.[9,10] Studies in Japanese, Chinese, Dutch, Arab and American cohorts suggest that a BglI and/or an MboI dimorphisms (located respectively in the first and ninth introns of the renin gene) may be associated with essential hypertension, stroke and diabetic nephropathy.[11-14]

More recently Fuchs and colleagues described two new polymorphisms in the enhancer region.[15] They went on to show that one of these (−5312 C/T) appears to influence in vitro gene expression—the T allele variant was associated with a 40% increase in renin gene transcription. A further study of a large community dwelling population (n=390) has shown that T allele carriers of the (−5312 C/T) polymorphism have significantly increased office and ambulatory blood pressures (mean difference 2-3 mm Hg).[16]

It is an object of the invention to provide a predictive assay for response to blood pressure lowering therapy.

STATEMENTS OF INVENTION

It has been surprisingly discovered that heterozygous or homozygous carriers of the T allele of the (C-5312T) renin single nucleotide polymorphism (SNP), i.e. those that have the polymorphism in one or both alleles of the renin gene, have a greater response to angiotensin-2-receptor blockers, ACE Inhibitors, aldosterone receptor blockers, and beta-receptor blockers, whereas those individuals that do not have the SNP present in either allele of the renin gene have a greater response to all renin inhibitors; calcium channel blockers; and diuretics.

Accordingly, the invention relates to a method of determining a suitable blood pressure lowering treatment for an individual, comprising a step of assaying a biological sample from the individual for the presence or absence of the C-5312T SNP in a distal enhancer region of the renin gene, wherein the presence of at least one T allele is indicative of an increased response to a blood pressure lowering treatment selected from the group comprising: angiotensin-2-receptor blockers; ACE Inhibitors; aldosterone receptor blockers; and beta-receptor blockers, and wherein the absence of a T allele (i.e homozygous for the C allele) is indicative of an increased response to a blood pressure lowering treatment selected from the group comprising: renin inhibitors; calcium channel blockers; and diuretics.

In other words, the presence of the SNP indicates that the individual is likely to respond better to the first group of drugs as compared to the second group of drugs, wherein response is defined as extent of BP lowering achieved.

Typically, the presence of at least one T allele is indicative of an increased response to a blood pressure lowering treatment selected from the group comprising: angiotensin-2-receptor blockers; ACE Inhibitors; and aldosterone receptor blockers.

Suitably, the presence of at least one T allele is indicative of an increased response to a blood pressure lowering treatment selected from the group comprising: angiotensin-2-receptor blockers; and ACE Inhibitors.

Ideally, the presence of at least one T allele is indicative of an increased response to a angiotensin-2-receptor blocker.

In one embodiment, the absence of the T allele is indicative of an increased response to renin inhibitors.

In one aspect, the presence of at least one T allele is indicative of an increased response to LOSARTAN. Typically, the absence of at least one T allele is indicative of an increased response to ALISKIREN.

Ideally, both alleles of the rennin gene are assayed for the presence of the SNP.

Any suitable biological sample which contains genetic material may be used as a biological sample for the assay of the present invention. Particularly suitable samples comprise saliva and leucocyte preparations.

In one embodiment, the individual is selected from the group comprising: individuals having established elevated blood pressure; individuals at risk of developing elevated blood pressure; and individuals identified as having elevated cardiovascular risk. However, the method of the invention may also be used with individuals that do not fall into any of the above-mentioned groups. Thus, for example, the pharmacogenomic assay of the present invention may form a part of a genetic screening assay of individuals that are not at risk of cardiovascular disease, high blood pressure, or hypertension.

An individual identified as carrying the SNP in at least one allele of the rennin gene is typically subjected to a heart disease risk factor management programme. Individuals found to be homozygous for the T allele (TT homozygotes) will ideally be subjected to an aggressive heart disease risk factor management programme.

In this specification, the term "heart disease risk factor management programme" should be taken to mean at least one of lifestyle management and pharmaceutical intervention, and wherein pharmaceutical intervention ideally includes treatment with at least one of RAAS blockade therapy, statin therapy, and anti-oxidant therapy.

The invention also relates to an assay kit for use in determining a suitable blood pressure lowering treatment for an individual and comprising:

means for detecting at least one allele of a C-5312T single nucleotide polymorphism in a biological sample from an individual; and instructions for determining a suitable blood pressure lowering agent for the individual, wherein the presence of at least one T allele is indicative of an increased response to a blood pressure lowering treatment selected from the group comprising: angiotensin-2-receptor blockers; ACE Inhibitors; aldosterone receptor blockers; and beta-receptor blockers, and wherein the absence of a T allele (i.e. CC homozygotes) is indicative of an increased response to a blood pressure lowering treatment selected from the group comprising: rennin inhibitors; calcium channel blockers; and diuretics.

In one embodiment, the instructions specify that the presence of at least one T allele is indicative of an increased response to a blood pressure lowering treatment selected from the group comprising: angiotensin-2-receptor blockers; ACE Inhibitors; and aldosterone receptor blockers.

Alternatively, the instructions may specify that presence of at least one T allele is indicative of an increased response to a blood pressure lowering treatment selected from the group comprising: angiotensin-2-receptor blockers; and ACE Inhibitors.

In a further embodiment, the instructions may specify that the presence of at least one T allele is indicative of an increased response to a angiotensin-2-receptor blocker.

Typically, the instructions specify that the absence of a T allele is indicative of an increased response to renin inhibitors.

Suitably, the instructions specify that the presence of at least one T allele is indicative of an increased response to LOSARTAN. Typically, the instructions specify that the absence of a T allele is indicative of an increased response to ALISKIREN.

The invention also relates to a method of predicting the likelihood of an individual having an atherothrombotic event, comprising the step of assaying a biological sample from the individual for the presence of a C-5312T single nucleotide polymorphism (SNP) in at least one allele of the distal enhancer region of the renin gene, wherein the presence of the SNP in at least one allele of the gene indicates that the individual is at an increased risk of having a future atherothrombotic event as compared to an individual homozygous for the C allele.

Typically, the biological sample from the individual is assayed for the presence of the C-5312T single nucleotide polymorphism (SNP) in both alleles of the distal enhancer region of the renin gene, wherein the presence of the SNP in both alleles of the gene (TT homozygous) indicates that the individual is at an increased risk of having a future atherothrombotic event as compared to an individual homozygous and/or heterozygous for the C allele.

Preferably, the method involves measuring the blood pressure of the individual, wherein the presence of the SNP in both alleles of the gene, combined with elevated blood pressure, indicates that the individual is at an increased risk of having a future atherothrombotic event.

Ideally, identified TT homzygotes are subjected to a heart disease risk factor management programme.

The invention also relates to an assay kit for use in identifying individuals at an increased risk of having a future atherothrombotic event, comprising:

means for detecting at least one allele of a C-5312T single nucleotide polymorphism in a biological sample from an individual; and instructions for determining the risk of the individual having a future atherothrombotic event, wherein the presence of the SNP in at least one allele of the gene indicates that the individual is at an increased risk of having a future atherothrombotic event as compared to an individual homozygous for the C allele.

Typically, the instructions specify that the presence of the SNP in both alleles of the gene (TT homozygous) indicates that the individual is at an increased risk of having a future atherothrombotic event as compared to an individual homozygous for the C allele.

Preferably, the instructions specify that the presence of the SNP in both alleles of the gene (TT homozygous) indicates that the individual is at an increased risk of having a future atherothrombotic event as compared to an individual heterozygous for the T allele.

Preferably, the instructions additionally specify measuring the blood pressure of the individual, wherein the presence of the SNP in one, and ideally both, alleles of the gene, combined with elevated blood pressure, indicates that the individual is at an increased risk of having a future atherothrombotic event compared with an individual homozygous or heterozygous for the C allele.

Examples of angiotensin-2-receptor blockers are losartan, irbesartan, telmesartan, candesartan.

Examples of ACE inhibitors are perindopril, enalopril, ramapril, and lisinopril.

Examples of beta-receptor blockers are metoprolol, and atenolol.

An example of an aldosterone receptor blocker is spironolactone.

Examples of calcium channel blockers are amlodipine, nifedipine, and felodipine.

Assay kits for detecting the presence or absence of the renin C-5312T SNP will be well known to those skilled in the art. For example, assay kits based on RT PCR will be known, as will suitable primers for use in such reactions. Assay kits that are not based on PCR technology are also known in the art. The design of probes for use in such kits is also within the ambit of the person skilled in the field of molecular biology. For example, WO 95/11995 describes the design and principles of use of arrays of oligonucleotide probes for use in genotyping SNP's, and in which the existence of a given SNP is manifested by differences in normalised hybridisation intensities of probes flanking the SNP when the probes hybridise to corresponding targets from different individuals. Further, Saiki et al[17] describe the design and use of allele-specific probes for analysing SNP's.

DETAILED DESCRIPTION OF THE INVENTION

Precise Location of the Renin Gene C-5312T Polymorphism

No information of this SNP in the NCBI database. The exact location of this polymorphism is −5312 base pairs upstream from the transcription start site (+1) (Fuchs et al.)[15]

Genotyping of the Renin Gene C-5312T Polymorphism

DNA was extracted from leukocytes by a salting out procedure as previously described.[18] DNA samples were relabelled with new identifier codes prior to any genotyping.

Genotyping of the renin gene C-5312T polymorphism, was performed using the Amplifluor technology[19] by KBio-Sciences Ltd (www.kbioscience.co.uk). In brief, genotyping is performed in 384-well microplates using a fluorescence resonance energy transfer (FRET)-based genotyping method. Amplification was initiated using the following allele-specific primers and a common downstream primer.

```
Allele specific 1 forward primer
                                (SEQUENCE ID NO. 1)
GAAGGTGACCAAGTTCATGCTGAACACCAAAGCAGGCTTAATCTGA Allele specific 2 forward primer
                                (SEQUENCE ID NO. 2)
GAAGGTCGGAGTCAACGGATTCACCAAAGCAGGCTTAATCTGG Common (allele 1 and 2) reverse primer
                                (SEQUENCE ID NO. 3)
AAAGCAGTCTCTGTAAGTGCCC
```

The allele-specific primers are tailed with unique sequences that create corresponding complementary sequences in the two amplicons. In the second round of amplification, quenched Universal Amplifluor™ primers (in a hairpin formation) are used. These primers contain 3' tails that specifically bind to the unique tailed sequences in the amplicons and continue amplification. In the final round of amplification, the action of the DNA polymerase opens up the hairpin structure and the quencher and reporter moieties are spatially separated. The excited reporter moiety emits either red or green fluorescence, the colour of which depends on which nucleotide is at the polymorphism site. The fluorescence is quantified by a microplate reader and then analysed via an Excel macro to provide genotypes for each SNP. 20 µL of total DNA was supplied to the company at 2 ng/µL (3 ng is consumed per assay) in "v-bottomed" 96-well micro-titre plates. Also included were a number of repeat (83) and blank samples (31) to check for reproducibility and to control for errors in sample handling.

Genetic Analysis Study

Using the above-described protocol, a genetic analysis study was carried out amongst a group of hypertensive patients participating in a clinical trial[20].

Table 1 shows the −5312 C/T SNP genotype frequencies amongst the hypertensive participants in the clinical trial compared to a community dwelling normal population. Despite similar allele frequencies, in contrast to the control normal population, the genotype distribution amongst the hypertensive population was clearly not in Hardy-Weinberg equilibrium, principally due to a paucity of TT homozygotes, and a small excess of CT heterozygotes. A likely explanation for the paucity of TT homozygotes is their exclusion from participation in the clinical trial. Relevant exclusion criteria for the trial included inability to withdraw from current antihypertensive medications, malignant hypertension and history of atherosclerotic coronary artery disease or cerebrovascular disease. Thus, it is the Applicants view that TT homozygotes, particularly in the presence of elevated BP, develop atherosclerotic complications earlier than CC homozygotes, or CT heterozygotes.

TABLE 1

−5312 C/T SNP genotype frequencies amongst the hypertensive participants in the clinical trial compared to a community dwelling control population

| Population | | SPP-100 hypertensives | Control population |
| --- | --- | --- | --- |
| N | | 259 | 387 |
| Genotype | CC | 166 (0.640) | 254 (0.66) |
| | CT | 92 (0.355) | 122 (0.31) |
| | TT | 1 (0.004) | 11 (0.03) |
| Allele proportion | C | 0.82 | 0.81 |
| | T | 0.18 | 0.19 |
| $\chi^2$ | | 10.06 ($p < 0.005$) | 1.344 ($p = 0.9$) |
| Hardy-Weinberg Equilibrium | | No | Yes |

Tables 2 and 3 show baseline clinic and ambulatory blood pressures, and the changes from baseline with study treatment. It is clear from these tables that BP lowering, particularly for sitting clinic pressures and night-time ambulatory BPs, was greatest with Losartan 100 mg daily amongst T allele carriers. This suggests that greater expression of renin contributes to the hypertension of T allele carriers, and through inhibition of the effects of the key end-product of the RAAS, namely angiotensin II, greater BP lowering was achieved.

There was a clear dose response relationship between the dose of Aliskiren and BP lowering, and in contrast to losartan, BP lowering was greatest amongst CC homozygotes. This was most obvious at the higher doses of aliskiren, 150 mg and 300 mg daily.

Table 4 shows the trough plasma renin activity (PRA) at baseline and after four weeks of treatment. Whilst PRA, at baseline, tended to be higher amongst T allele carriers, this did not achieve statistical significance. As expected, Losartan therapy resulted in increased PRA levels, whilst Aliskiren suppressed PRA. With both therapies PRA tended to be higher amongst T-allele carriers.

Table 4 also shows trough plasma aliskiren levels after 4 weeks of treatment. Interestingly on treatment plasma aliskiren levels were reduced by about 20%-30% amongst T allele carriers. The likely explanation for this decrease in drug level is that T allele carriers respond to renin inhibition and to the resultant decrease in negative feed-back by angiotensin II on the RAAS, by greatly increased expression of the renin gene by comparison to CC homozygotes. There is a strong affinity between renin protein and Aliskiren (Aliskiren IC50=0.6 nM=0.4 ng/ml). The excess renin produced by T allele carriers binds the drug strongly and reduces the free drug concentration. Given that unstimulated plasma renin levels range from 10-20 pg/ml, plasma renin levels in the presence of aliskiren 160-640 mg range from 300-600 pg/ml (Nussberger et al. Hypertens 2002; 39:e1-e8), and that plasma aliskiren levels were reduced from 31.9 ng/ml amongst CC homozygotes taking Aliskiren 300 mg daily, to 20.5 ng/ml amongst T allele carriers, it appears likely that much of excess renin and much of the aliskiren trapping occurred at tissue rather than plasma level. In any case the reduction of plasma Aliskiren amongst T allele carriers provides at least part of the explanation for the reduced BP lowering efficacy of Aliskiren amongst these patients.

TABLE 2

Baseline clinic blood pressures, and changes from baseline with study treatment.

| Haemodyamic parameter | | Aliskiren 37.5 mg (T/C 11/29) | Aliskiren 75 mg (T/C 17/25) | Aliskiren 150 mg (T/C 16/25) | Aliskiren 300 mg (T/C 15/27) | Losartan 100 mg (T/C 15/24) |
|---|---|---|---|---|---|---|
| Sitting SBP | | | | | | |
| Tallele carriers | baseline | 153.5 ± 18.8 | 153.1 ± 20.5 | 154.6 ± 18.5 | 157.7 ± 14.5 | 162.0 ± 14.6 |
|  | change | 1.45 ± 12.4 (3.7) | −2.24 ± 18.2 (3.9) | −2.1 ± 20.6 (3.6) | −7.6 ± 15.3 (4.0) | −14.5 ± 18.5 (4.8) |
| CC homozygotes | baseline | 157.8 ± 17.0 | 160.4 ± 16.3 | 163.1 ± 17.7 | 158.9 ± 17.2 | 157.6 ± 14.8 |
|  | change | −7.48 ± 18.2 (3.4) | −6.82 ± 15.9 (2.2) | −12.8 ± 17.6 (2.5) | −14.8 ± 14.6 (2.8) | −8.4 ± 20.8 (4.3) |
| Sitting DBP | | | | | | |
| Tallele carriers | baseline | 95.0 ± 8.4 | 88.7 ± 10.3 | 94.0 ± 11.0 | 95.9 ± 8.3 | 93.3 ± 9.3 |
|  | change | −2.1 ± 9.5 (2.8) | −0.47 ± 14.3 (3.5) | −1.8 ± 11.3 (2.0) | −2.9 ± 7.6 (2.0) | −5.9 ± 13.4 (3.5) |
| CC homozygotes | baseline | 92.3 ± 12.1 | 96.3 ± 11.3 | 92.3 ± 9.1 | 94.5 ± 11.7 | 96.6 ± 7.5 |
|  | change | −2.3 ± 11.2 (2.1) | −0.48 ± 11.2 (2.2) | −3.2 ± 9.5 (1.3) | −8.4 ± 11.5 (2.2) | −4.7 ± 8.4 (1.7) |
| Standing SBP | | | | | | |
| Tallele carriers | baseline | 154.1 ± 22.2 | 147.9 ± 20.5 | 157.1 ± 21.2 | 160.5 ± 16.2 | 158.1 ± 21.2 |
|  | change | 1.18 ± 12.2 (3.7) | −4.96 ± 13.2 (2.8) | −5.6 ± 22.2 (3.9) | −8.6 ± 14.3 (3.7) | −6.7 ± 22.6 (5.8) |
| CC homozygotes | baseline | 159.1 ± 15.5 | 164.6 ± 21.5 | 161.5 ± 17.9 | 161.8 ± 19.2 | 159.9 ± 16.2 |
|  | change | −6.6 ± 16.4 (3.0) | −3.41 ± 11.5 (2.6) | −12.8 ± 15.5 (2.2) | −16.22 ± 13.2 (2.5) | −9.3 ± 21.5 (4.4) |
| Standing DBP | | | | | | |
| Tallele carriers | baseline | 94.9 ± 10.4 | 89.4 ± 11.7 | 98.7 ± 9.0 | 99.8 ± 12.9 | 97.8 ± 12.4 |
|  | change | 3.4 ± 9.1 (2.9) | −0.4 ± 10.3 (2.5) | −4.8 ± 10.2 (1.8) | −6.6 ± 9.6 (2.5) | −7.9 ± 15.8 (4.1) |
| CC homozygotes | baseline | 97.5 ± 13.4 | 101.8 ± 12.9 | 94.8 ± 10.9 | 100.5 ± 10.7 | 101.6 ± 10.2 |
|  | change | −3.2 ± 12.1 (2.2) | −0.8 ± 11.5 (2.3) | −1.6 ± 10.3 (1.4) | −9.7 ± 13.4 (2.6) | −6.8 ± 10.1 (2.1) |

Data expressed as mean ± SD (SEM)

TABLE 3

Baseline ambulatory blood pressures, and changes from baseline with study treatment.

| Haemodyamic parameter | | Aliskiren 37.5 mg (T/C 11/29) | Aliskiren 75 mg (T/C 17/25) | Aliskiren 150 mg (T/C 16/25) | Aliskiren 300 mg (T/C 15/27) | Losartan 100 mg (T/C 15/24) |
|---|---|---|---|---|---|---|
| Day SBP | | | | | | |
| Tallele carriers | baseline | 147.1 ± 15.3 | 153.5 ± 9.6 | 157.4 ± 12.8 | 150.5 ± 9.3 | 152.4 ± 10.7 |
|  | change | −0.7 ± 5.9 (1.8) | −7.0 ± 13.6 (0.9) | −6.1 ± 9.6 (1.7) | −10.2 ± 8.6 (2.3) | −11.4 ± 15.1(3.9) |
| CC homozygotes | baseline | 156.0 ± 10.4 | 154.4 ± 11.7 | 155.4 ± 9.3 | 154.3 ± 9.7 | 152.0 ± 8.2 |
|  | change | −1.8 ± 12.5 (2.3) | −4.0 ± 3.9 (2.7) | −8.6 ± 11.5 (1.6) | −11.9 ± 12.4 (2.4) | −10.5 ± 10.8(2.2) |
| Day DBP | | | | | | |
| Tallele carriers | baseline | 92.4 ± 12.0 | 92.4 ± 8.8 | 99.0 ± 8.6 | 92.1 ± 7.3 | 90.7 ± 9.5 |
|  | change | −0.2 ± 5.1 (1.5) | −2.9 ± 3.8 (0.9) | −4.7 ± 6.2 (1.1) | −4.9 ± 7.8 (2.1) | −6.4 ± 10.4 (2.7) |
| CC homozygotes | baseline | 94.5 ± 12.1 | 95.0 ± 10.5 | 94.1 ± 9.4 | 94.0 ± 9.7 | 92.5 ± 8.8 |
|  | change | −0.1 ± 9.1 (1.7) | −2.7 ± 6.51(1.3) | −4.9 ± 6.2 (0.9) | −7.9 ± 8.1 (1.6) | −5.8 ± 8.1 (1.7) |
| Night SBP | | | | | | |
| Tallele carriers | baseline | 124.5 ± 13.7 | 133.3 ± 16.1 | 131.3 ± 16.0 | 130.5 ± 14.4 | 138.4 ± 13.3 |
|  | change | −1.4 ± 7.8 (2.4) | −5.3 ± 12.5 (2.0) | −4.4 ± 13.3 (2.3) | −6.5 ± 8.8 (2.3) | −12.9 ± 14.3 (3.7) |
| CC homozygotes | baseline | 129.9 ± 13.8 | 130.6 ± 15.2 | 132.5 ± 13.8 | 131.6 ± 11.4 | 131.2 ± 11.7 |
|  | change | 2.1 ± 14.5 (2.7) | −5.6 ± 8.0 (2.5) | −7.9 ± 10.2 (1.5) | −12.1 ± 9.9 (1.9) | −7.1 ± 12.2 (2.5) |
| Night DBP | | | | | | |
| Tallele carriers | baseline | 74.3 ± 10.7 | 76.6 ± 10.4 | 78.6 ± 11.0 | 77.4 ± 12.3 | 80.0 ± 10.8 |
|  | change | −0.3 ± 6.5 (2.0) | −3.3 ± 5.7 (1.41) | −4.1 ± 7.3 (1.3) | −4.1 ± 7.8 (2.1) | −7.9 ± 9.4 (2.4) |
| CC homozygotes | baseline | 74.5 ± 11.0 | 77.8 ± 12.3 | 76.4 ± 11.3 | 76.5 ± 8.7 | 77.2 ± 11.8 |
|  | change | 2.7 ± 9.4 (1.8) | −2.7 ± 8.2 (1.6) | −4.9 ± 7.7 (1.1) | −8.0 ± 8.2 (1.6) | −4.2 ± 8.0 (1.8) |

Data expressed as mean ± SD (SEM)

TABLE 4

Trough plasma aliskiren levels and trough plasma renin activity at baseline and after four weeks of treatment.

| Parameter | Screened only (T/C 13/29) | Aliskiren 37.5 mg (T/C 10/29) | 75 mg (T/C 16/23) | 150 mg (T/C 15/25) | 300 mg (T/C 16/23) | Losartan 100 mg (T/C 15/24) |
|---|---|---|---|---|---|---|
| Plasma aliskiren on treatment (ng/ml) | | | | | | |
| Ren CC homozygotes | | 3.1 (4.0, 1.5) | 4.4 (6.4, 3.5) | 11.0 (16.0, 6.7) | 31.5 (70.3, 13.5) | — |

TABLE 4-continued

Trough plasma aliskiren levels and trough plasma renin activity at baseline and after four weeks of treatment.

| Parameter | Screened only (T/C 13/29) | Aliskiren 37.5 mg (T/C 10/29) | 75 mg (T/C 16/23) | 150 mg (T/C 15/25) | 300 mg (T/C 16/23) | Losartan 100 mg (T/C 15/24) |
|---|---|---|---|---|---|---|
| Ren T allele carriers | | 2.4 (2.9, 1.1) | 3.9 (7.3, 2.8) | 7.1 (12.0, 5.4) | 20.5 (41.0, 17.0) | — |
| PRA at baseline (ng/ml/h) | | | | | | |
| Ren CC homozygotes | 1.1 (0.48, 1.4) | 0.71 (0.21, 1.20) | 0.62 (0.26, 1.10) | 0.56 (0.30, 1.20) | 0.83 (0.45, 1.87) | 0.75 (0.45, 1.27) |
| Ren T allele carriers | 1.1 (0.48, 1.9) | 0.36 (0.24, 1.10) | 1.10 (0.72, 1.52) | 0.79 (0.48, 1.60) | 0.86 (0.49, 1.90) | 0.95 (0.34, 1.40) |
| PRA on treatment (ng/ml/h) | | | | | | |
| Ren CC homozygotes | | 0.32 (0.12, 0.77) | 0.16 (0.09, 0.46) | 0.10 (0.06, 0.31) | 0.17 (0.06, 0.42) | 1.65 (0.60, 3.20) |
| Ren T allele carriers | | 0.17 (0.06, 0.89) | 0.42 (0.20, 0.59) | 0.17 (0.12, 0.47) | 0.18 (0.06, 0.51) | 1.80 (0.65, 3.30) |
| PRA Percentage Change (%) | | | | | | |
| Ren CC homozygotes | | −50.0 (−4.5, −62.7) | −61.7 (−32.7, −82.1) | −77.8 (−70.6, −84.8) | −82.5 (−69.9, −86.7) | 110.32 (15.4, 262.5) |
| Ren T allele carriers | | −63.8 (−11.2, −77.9) | −54.3 (−44.4, −81.5) | −75.7 (−67.4, −82.1) | −82.5 (−69.9, −86.7) | 97.6 (22.2, 363.8) |

Data expressed as median (interquartile range).
All available data are shown - Baseline PRA, on-treatment PRA and % change in PRA values were available for 39, 39, 40, 39 and 39 subjects in the five treatment groups - (Aliskiren 37.5, 75, 150, 300; and Losartan 100) respectively.

Conclusions

The data clearly illustrate that BP lowering is considerably greater
   amongst T allele carriers of the −5312 C/T variant, with the angiotensin receptor blocker, Losartan,
   amongst CC homozygotes of the −5312 C/T variant, with the renin inhibitor, Aliskiren.

INDUSTRIAL APPLICATION

Laboratory/Desktop/Bedside testing for the distal enhancer renin gene -5312 C/T SNP single nucleotide polymorphism;
   testing will allow patient specific prescribing of the most effective blocker of the renin angiotensin aldosterone system at the correct dose. This will lead to the following benefits
   Effective reduction of BP in a larger proportion of patients,
   Reduced adverse events—through individualised prescribing of the correct RAAS blocker for each patient, patients who are unlikely to benefit from a particular drug will not be exposed to its potentially harmful effects.
   Drug cost savings (state or individual cost savings)—The test will sensitively and specifically identify those patients who are likely and those who are unlikely to gain direct benefit from particular drug classes. Patients who are unlikely to benefit from a particular drug will not be prescribed unnecessary therapy.
   Patient and physician time savings—through reduction/elimination of the current process of trial and error prescribing, the number of follow-up visits to the doctor needed to achieve BP control could be considerably reduced, even halved.

The invention is not limited to the embodiment hereinbefore described which may be varied in construction, detail and process step without departing from the spirit of the invention.

REFERENCES

1. Oparil S, Haber The renin angiotensin system N Engl J Med; 292: 381-401/446-457.
2. Yusef S, Sleight P, Pogue J, Bosch J, Davies R, Dagenais G. Effects of an angiotensin converting enzyme inhibitor, ramipril, on cardiovascular events in high-risk patients: the Heart Outcomes Prevention Evaluation Study Investigators. N Engl J Med 2000; 342: 145-153.
3. Ross R. The pathogenesis of atherosclerosis: a perspective for the 1990s. Nature 1993; 362: 801-809.
4. Dzau V J. Tissue angiotensin and pathobiology of vascular disease, a unifying hypothesis. Hypertension 2001; 37: 1047-1052.
5. Bader M. Ganten D. Regulation of renin: new evidence from cultured cells and genetically modified mice. J. Mol. Med 2000; 78:130-9.
6. Takahashi S. Takahashi K. Kaneko T. Ogasawara H. Shindo S. Kobayashi M. Human renin-binding protein is the enzyme N-acetyl-D-glucosamine 2-epimerase. J. Biochem 1999; 125:348-53.
7. Halushka M K, Fan J B, Bently K, Hsie L, Shen N, Weder A, Cooper R, Lipshutz R, Chakravarti A. Patterns of SNPs in candidate genes for BP homeostasis. Nature Genetics 1999; 22: http://chakravarti.som.jhmi.edu/candidates/candidates.html.
8. Nagy Z. Busjahn A. Bahring S. Faulhaber HD. Gohlke HR. Knoblauch H. Rosenthal M. Muller-Myhsok B. Schuster H. Luft F C. Quantitative trait loci for blood pressure exist near the IGF-1, the Liddle syndrome, the angiotensin II-receptor gene and the renin loci in man. J. Am. Soc. Nephrol. 1999; 10:1709-16.
9. Niu T. Xu X. Cordell H J. Rogus J. Zhou Y. Fang Z. Lindpaintner K. Linkage analysis of candidate genes and gene-gene interactions in chinese hypertensive sib pairs. Hypertens 1999; 33:1332-7.
10. Kainulainen K. Perola M. Terwilliger J. Kaprio J. Koskenvuo M. Syvanen A C. Vartiainen E. Peltonen L. Kontula K. Evidence for involvement of the type 1 angiotensin II receptor locus in essential hypertension. Hypertension 1999; 33:844-9.

11. Chiang F T. Hsu KL. Tseng C D. Lo HM. Chern TH. Tseng Y Z. Association of the renin gene polymorphism with essential hypertension in a Chinese population. Clin Genet 1997; 51:370-4.

12. JunFrossard PM. Lestringant GG. Malloy MJ. Kane JP. Human renin gene BglI dimorphism associated with hypertension in two independent populations. Clin Gen 1999; 56:428-33.

13. Frossard PM. Malloy MJ. Lestringant GG. Kane JP. Haplotypes of the human renin gene associated with essential hypertension and stroke. J. Hum. Hypertens. 2001; 15: 49-55.

14. Deinum J. Tarnow L. van Gool JM. de Bruin RA. Derkx FH. Schalekamp M A. Parving HH. Plasma renin and prorenin and renin gene variation in patients with insulin-dependent diabetes mellitus and nephropathy. Nephrology Dialysis Transplantation 1999; 14:1904-11.

15. Fuchs S; Philippe J; Germain S; Mathieu F; Jeunemaitre; X, Corvol P; Pinet F. Functionality of two new polymorphisms in the human renin gene enhancer region. Journal of Hypertension 20(12): 2391-2398; December 2002

16. N Moore, M Stojanovic, S Lyons, E O'Brien, D Shields, J O'Brien, A Stanton. A newly discovered polymorphism in the renin gene enhancer region is associated with elevated ambulatory BP levels in a large community population. Abstract International Society of Hypertension 2004.

17. Saiki et al., Nature 324, 163-166 (1986)

18. S A Miller, D. D. D., and H F Polesky, simple salting out procedure for extracting DNA from human nucleated cells. Nucleic Acids Res., 1988. 16(3): p. 1215.

19. I. A. Nazarenko, e.a., A closed tube format for amplification and detection of DNA based on energy transfer. Nucleic Acids Research, 1997. 25: p. 2516-21.

20. Stanton A, Jensen C, Nussberger J, O'Brien E. Blood pressure lowering in essential hypertension with an oral renin inhibitor, aliskiren. Hypertension 2003; 42:1137-43.

The invention claimed is:

1. A method for administering a suitable blood pressure lowering treatment to an individual, comprising the steps of assaying a biological sample from the individual for the presence of a C-5312T single nucleotide polymorphism (SNP) in a distal enhancer region of the renin gene, wherein both alleles of the renin gene are assayed;

determining a suitable blood pressure lowering treatment for the individual based on the presence or absence of a T allele;

and administering the suitable blood pressure lowering treatment to the individual,
   wherein the presence of one or two T alleles indicates that the suitable blood pressure lowering treatment is an angiotensin-2-receptor blocker or an ACE inhibitor,
   and the presence of two C alleles indicates that the suitable blood pressure lowering treatment is a calcium channel blocker.

2. A method as claimed in claim 1 in which the angiotensin-2-receptor blocker is LOSARTAN.

3. A method as claimed in claim 1 in which the biological sample from the individual is saliva or leucocytes.

4. A method as claimed in claim 1 in which the individual is selected from the group consisting of: individuals having established elevated blood pressure; individuals at risk of developing elevated blood pressure; and
   individuals identified as having elevated cardiovascular risk.

5. A method as claimed in claim 1 in which an individual having one or two T alleles is further subjected to a heart disease risk factor management programme including lifestyle management.

* * * * *

SEQUENCE LISTING

```
<160> NUMBER OF SEQ ID NOS: 3

<210> SEQ ID NO 1
<211> LENGTH: 46
<212> TYPE: DNA
<213> ORGANISM: Artificial Sequence
<220> FEATURE:
<221> NAME/KEY: misc_feature
<222> LOCATION: (1)..(46)
<223> OTHER INFORMATION: Allele specific 1 forward primer

<400> SEQUENCE: 1
gaaggtgacc aagttcatgc tgaacaccaa agcaggctta atctga          46

<210> SEQ ID NO 2
<211> LENGTH: 43
<212> TYPE: DNA
<213> ORGANISM: Artificial Sequence
<220> FEATURE:
<221> NAME/KEY: misc_feature
<222> LOCATION: (1)..(43)
<223> OTHER INFORMATION: Allele specific 2 forward primer

<400> SEQUENCE: 2
gaaggtcgga gtcaacggat tcaccaaagc aggcttaatc tgg             43

<210> SEQ ID NO 3
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Common reverse primer

<400> SEQUENCE: 3
aaagcagtct ctgtaagtgc cc                                     22
```